Feb. 8, 1966 H. M. TIRET Plant Pat. 2,600
FUCHSIA PLANT
Filed Nov. 23, 1964
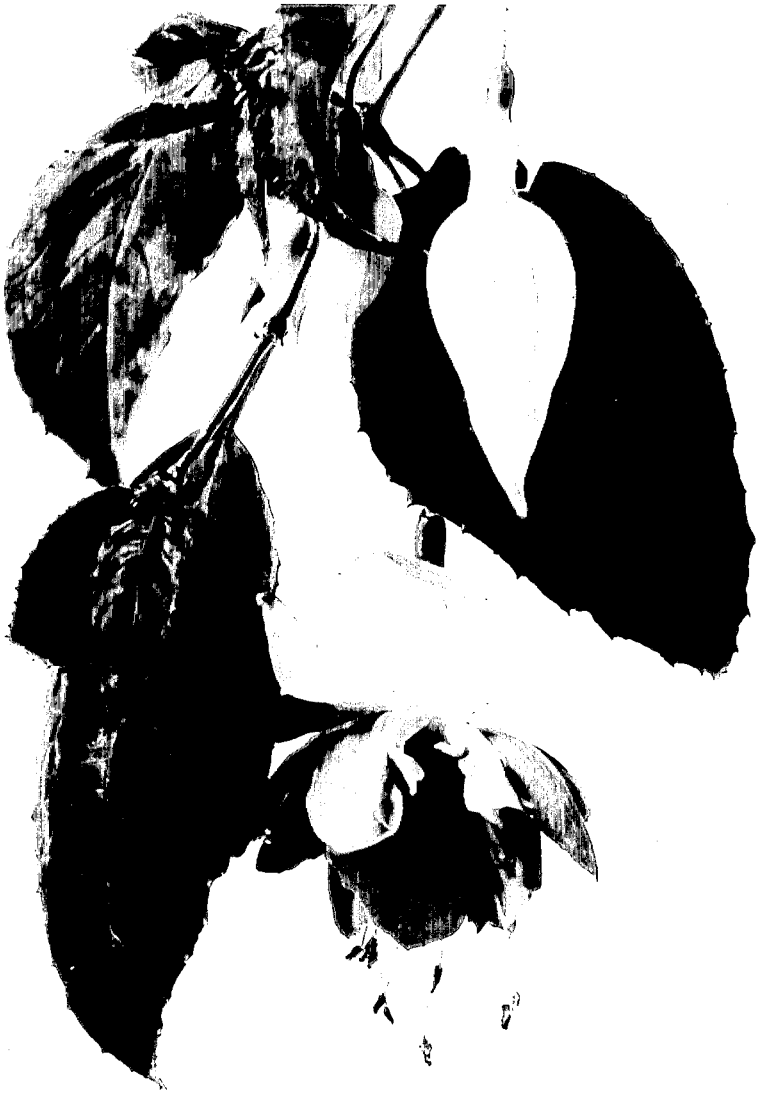

United States Patent Office

Plant Pat. 2,600
Patented Feb. 8, 1966

2,600
FUCHSIA PLANT

Horace M. Tiret, 2225 Taraval St.,
San Francisco, Calif.

Filed Nov. 23, 1964, Ser. No. 413,385
1 Claim. (Cl. Plt.—84)

This invention relates to a new and improved fuchsia plant, the principal new and different characteristic of which is the exceptional size of flower combined with white flushed pink sepals and an unusual colored corolla, having an excellent trailing habit of growth unlike any other fuchsia plant.

The accompanying drawing illustrates the plant in bloom and the aforementioned new and different characteristics.

The fuchsia plant was derived as a hybrid from a seedling (unpatented) not introduced to the trade, namely 14–42–8 (figures representing applicant's own breeding symbols) and a seedling (unpatented) not introduced to the trade, namely 15–41–6. The plant has been annually reproduced at Colma, California, by cuttings which retained the characteristics of the parent fuchsia plant.

The plant has a vigorous, trailing habit of growth. It is a heavy bloomer producing many large flowers. The petals of a mature flower are Rose Bengal (British Horticultural Color Chart #25/1) outer petals marbled with Rose Bengal #25/3. When flower first grows petals are orchid purple #31/1 and outer petals are marbled with orchid purple #31/3. As flower matures petals flare outward gracefully. It gives the effect of two distinct flowers on the same plant.

In the accompanying drawing, the figure shows a typical branch tip represented in approximate actual size.

A detailed description of the new variety of fuchsia plant follows (all measurements approximate):

*Habit of growth.*—Trailing, early, consistent bloomer and self-brancher.

*Foliage.*—The leaves are dark green, large in size, medium veined surface. The mature leaf is approximately 4½″ in length and 2½″ in width at the broadest point.

Texture of the leaf is crinkly (medium). Branches are dark green flushed slightly with reddish-brown.

*Buds.*—Color of buds is greenish white, acquiring pinkish white cast when mature. Length from ovary is approximately 2¼″. Width at the broadest point is 1⅛″.

*Ovary.*—Color of the ovary is solid green. Length is ½″. Width at the broadest point, at maturity, is 5/16″.

*Sepals.*—Topside is white flushed with Bengal Rose #25/3 and #25/2. Texture is smooth. Underside is the same color as topside, except texture is crepelike. Sepals are semi-broad and long, flaring horizontally from base of flower. They are four in number, 2¼″ in length and ⅝″ in width at widest point.

*Tube.*—Medium short. Length is approximately ¾″, width ⅜″ at widest point. The tube is white.

*Stamens.*—Eight in number, colored rose and rose-purple anthers. Medium slender, 2½″ in length.

*Pistil.*—The style is approximately 3¼″ in length from the ovary to its tip. In width it is 1/16″. The color is white with creamy white stigma.

*Petals.*—The petals number approximately 22. They are exceptionally large, fully open corolla. The corolla is flaring in form when fully mature, giving an irregular but distinct appearance. The diameter of the fully open mature flower is approximately 3¼″. The large mature petals are approximately 1½″ in length and 1½″ in width. They have a smooth appearance.

*Parentage.*—Applicant's own seedlings (unpatented) not introduced to the trade, applicant's seedling symbols 14–42–8 and 15–41–6.

Having thus disclosed my discovery, I claim:

A new and distinct variety of fuchsia plant herein described and illustrated, characterized by the exceptional size of the flower, unusual color of the petals when flower first opens as contrasted with color of petals of mature flower and distinct flaring form, which constitute a fuchsia unlike any other of its type.

No references cited.

ABRAHAM G. STONE, *Primary Examiner.*